(12) United States Patent
Chuter

(10) Patent No.: US 11,033,384 B2
(45) Date of Patent: Jun. 15, 2021

(54) AORTIC VALVE STENT GRAFT

(71) Applicant: COOK MEDICAL TECHNOLOGIES LLC, Bloomington, IN (US)

(72) Inventor: Timothy A M Chuter, San Francisco, CA (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 192 days.

(21) Appl. No.: 16/136,937

(22) Filed: Sep. 20, 2018

(65) Prior Publication Data

US 2019/0015201 A1 Jan. 17, 2019

Related U.S. Application Data

(63) Continuation of application No. 13/287,690, filed on Nov. 2, 2011, now Pat. No. 10,105,218, which is a
(Continued)

(51) Int. Cl.
*A61F 2/24* (2006.01)
*A61F 2/07* (2013.01)
(Continued)

(52) U.S. Cl.
CPC ............... *A61F 2/2418* (2013.01); *A61F 2/07* (2013.01); *A61F 2/95* (2013.01); *A61F 2/2436* (2013.01);
(Continued)

(58) Field of Classification Search
CPC .. A61F 2/2418; A61F 2220/0016; A61F 2/24; A61F 2/2427
See application file for complete search history.

(56) References Cited

U.S. PATENT DOCUMENTS 6,168,619 B1 1/2001 Dinh et al.
6,245,102 B1 6/2001 Jayaraman
(Continued)

FOREIGN PATENT DOCUMENTS

DE 102007045188 6/2008
EP 1264582 12/2002
(Continued)

OTHER PUBLICATIONS

Sisman, Mehtap et al., The Comparison between Self-Expanding and Balloon Expandable Stent Results in Left Anterior Descending Artery, International Journal of Angiology, Jan. 2001, pp. 34-40, vol. 10, No. 1, Springer New York Link Date Feb. 19, 2004.
(Continued)

*Primary Examiner* — Christopher D. Prone
(74) *Attorney, Agent, or Firm* — Brinks Gilson & Lione

(57) ABSTRACT

An implantable endoluminal prosthesis for replacing a damaged aortic valve is provided. In one embodiment, the prosthesis includes a balloon-expandable stent, a tubular conduit that extends into the ascending aorta, and a self-expanding stent. The tubular conduit extends across the balloon-expandable stent. The tubular conduit includes an artificial valve. The self-expanding stent extends across the tubular conduit into the ascending aorta. The balloon-expandable stent, the tubular conduit, and the self-expanding stent are coupled to provide unidirectional flow of fluid into the aorta and further into the coronary arteries. Also provided is a method for implanting the endoluminal prosthesis.

20 Claims, 8 Drawing Sheets

Related U.S. Application Data continuation of application No. 12/264,740, filed on Nov. 4, 2008, now Pat. No. 8,715,337.

(60) Provisional application No. 60/986,908, filed on Nov. 9, 2007.

(51) Int. Cl.
*A61F 2/95* (2013.01)
*A61F 2/90* (2013.01)

(52) U.S. Cl.
CPC ........... *A61F 2/90* (2013.01); *A61F 2002/075* (2013.01); *A61F 2220/005* (2013.01); *A61F 2220/0016* (2013.01); *A61F 2220/0058* (2013.01); *A61F 2230/005* (2013.01); *A61F 2230/008* (2013.01); *A61F 2230/0054* (2013.01); *A61F 2230/0067* (2013.01); *A61F 2250/006* (2013.01); *A61F 2250/0007* (2013.01); *A61F 2250/0048* (2013.01)

(56) References Cited

U.S. PATENT DOCUMENTS

| | | |
|---|---|---|
| 6,254,642 B1 | 7/2001 | Taylor |
| 6,258,120 B1 | 7/2001 | McKenzie et al. |
| 6,409,756 B1 | 6/2002 | Murphy |
| 6,416,544 B2 | 7/2002 | Sugita et al. |
| 6,425,916 B1 | 7/2002 | Garrison et al. |
| 6,494,909 B2 | 12/2002 | Greenhalgh |
| 6,730,118 B2 | 5/2004 | Spenser et al. |
| 6,773,453 B2 | 8/2004 | Ravenscroft |
| 6,773,454 B2 | 8/2004 | Wholey et al. |
| 6,797,000 B2 | 9/2004 | Simpson et al. |
| 6,911,040 B2 | 6/2005 | Johnson et al. |
| 7,018,404 B2 | 3/2006 | Holmberg et al. |
| 7,144,421 B2 | 12/2006 | Carpenter et al. |
| 7,192,442 B2 | 3/2007 | Solem et al. |
| 7,220,274 B1 | 5/2007 | Quinn |
| 7,351,256 B2 | 4/2008 | Hojeibane et al. |
| 7,377,938 B2 | 5/2008 | Sarac et al. |
| 7,442,204 B2 | 10/2008 | Schwammenthal et al. |
| 7,510,574 B2 | 3/2009 | Le et al. |
| 7,556,643 B2 | 7/2009 | Casey, II et al. |
| 7,572,286 B1 | 8/2009 | Chen et al. |
| 7,591,848 B2 | 9/2009 | Allen |
| 7,682,390 B2 | 3/2010 | Seguin |
| 7,780,726 B2 | 8/2010 | Seguin |
| 7,789,909 B2 | 9/2010 | Andersen et al. |
| 7,799,072 B2 | 9/2010 | Greenberg |
| 7,806,920 B2 | 10/2010 | Duran |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,967,853 B2 | 6/2011 | Eidenschink et al. |
| 8,016,877 B2 | 9/2011 | Seguin et al. |
| 8,080,054 B2 | 12/2011 | Rowe |
| 8,092,521 B2 | 1/2012 | Figulla et al. |
| 8,167,934 B2 | 5/2012 | Styrc et al. |
| 8,206,437 B2 | 6/2012 | Bonhoeffer et al. |
| 8,206,438 B2 | 6/2012 | Yang et al. |
| 8,348,996 B2 | 1/2013 | Tuval et al. |
| 2003/0120333 A1 | 6/2003 | Ouriel et al. |
| 2003/0130726 A1 | 7/2003 | Thorpe et al. |
| 2003/0199967 A1 | 10/2003 | Hartley et al. |
| 2004/0044402 A1 | 3/2004 | Jung et al. |
| 2004/0117003 A1 | 6/2004 | Ouriel et al. |
| 2004/0236411 A1 | 11/2004 | Sarac et al. |
| 2004/0254636 A1 | 12/2004 | Flagle et al. |
| 2005/0075725 A1 | 4/2005 | Rowe |
| 2005/0085900 A1* | 4/2005 | Case ................. A61F 2/2475 623/1.24 |
| 2005/0096736 A1 | 5/2005 | Osse et al. |
| 2005/0102018 A1 | 5/2005 | Carpenter et al. |
| 2005/0137682 A1 | 6/2005 | Justino |
| 2005/0182483 A1 | 8/2005 | Osborne et al. |
| 2005/0222674 A1 | 10/2005 | Paine et al. |
| 2005/0251251 A1 | 11/2005 | Cribier |
| 2006/0149360 A1 | 7/2006 | Schwammenthal et al. |
| 2006/0195180 A1 | 8/2006 | Kheradvar et al. |
| 2006/0265056 A1 | 11/2006 | Nguyen et al. |
| 2006/0276813 A1 | 12/2006 | Greenberg |
| 2007/0123972 A1 | 5/2007 | Greenberg et al. |
| 2007/0168013 A1 | 7/2007 | Douglas |
| 2007/0173926 A1 | 7/2007 | Bobo, Jr. et al. |
| 2007/0213813 A1 | 9/2007 | Von Segesser et al. |
| 2007/0239273 A1 | 10/2007 | Allen |
| 2007/0244546 A1 | 10/2007 | Francis |
| 2007/0282436 A1 | 12/2007 | Pinchuk |
| 2008/0039891 A1 | 2/2008 | McGuckin, Jr. et al. |
| 2008/0082166 A1 | 4/2008 | Styrc et al. |
| 2008/0208314 A1 | 8/2008 | Skerven |
| 2008/0262593 A1 | 10/2008 | Ryan et al. |
| 2008/0275549 A1 | 11/2008 | Rowe |
| 2009/0099649 A1 | 4/2009 | Chobotov et al. |
| 2009/0171437 A1 | 7/2009 | Brocker et al. |
| 2010/0063577 A1 | 3/2010 | Case et al. |
| 2010/0094411 A1 | 4/2010 | Tuval et al. |
| 2010/0168839 A1 | 7/2010 | Braido et al. |
| 2010/0256738 A1 | 10/2010 | Berglund |
| 2010/0298927 A1 | 11/2010 | Greenberg |
| 2011/0208289 A1 | 8/2011 | Shalev |
| 2012/0053676 A1 | 3/2012 | Ku et al. |
| 2012/0116498 A1 | 5/2012 | Chuter et al. |
| 2012/0130478 A1 | 5/2012 | Shaw |
| 2012/0283820 A1 | 11/2012 | Tseng et al. |

FOREIGN PATENT DOCUMENTS

| | | |
|---|---|---|
| WO | WO2003/003943 | 1/2003 |
| WO | WO2005/011535 | 2/2005 |
| WO | WO2006/127765 | 11/2006 |
| WO | WO2008/070797 | 6/2008 |
| WO | WO2010/008549 | 1/2010 |
| WO | WO2010/098857 | 9/2010 |
| WO | WO2012/039753 | 3/2012 |

OTHER PUBLICATIONS

International Search Report and Written Opinion for PCT/US2008/012500, dated Feb. 6, 2009, pp. 1-15.
International Search Report and Written Opinion for PCT/US2008/012500 dated Feb. 6, 2009, 15 pgs.
Sisman, Mehtap et al., "The Comparison Between Self-Expanding and Balloon Expandable Stent Results in Left Anterior Descending Artery", International Journal of Angiology, Jan. 2001, pp. 34-40, vol. 10, No. 1, springer New York, springer Link Date Feb. 19, 2004, 2 pgs.
Extended European Search Report for EP11275139 dated Oct. 8, 2012, 12 pgs.
Notice of Loss of Rights for EP11275139 dated Jun. 13, 2013, 1 pg.
Response to Notice of Loss of Rights for EP11275139 dated Aug. 12, 2013, 11 pgs.
Patent Examination Report No. 1 for AU2011244968 dated Dec. 23, 2012, 3 pgs.
Response to Patent Examination Report No. 1 for AU2011244968 dated Oct. 17, 2013, 11 pgs.
Patent Examination Report No. 2 for AU2011244968 dated Oct. 22, 2013, 3 pgs.
Response to Patent Examination Report No. 2 for AU2011244968 dated Dec. 20, 2013, 7 pgs.
Patent Examination Report No. 3 for AU2011244968 dated Jan. 14, 2014, 4 pgs.
Patent Examination Report No. 1 for AU2011244966 dated Dec. 23, 2012, 3 pgs.
Response to Patent Examination Report No. 1 for AU2011244966 dated Jan. 22, 2014, 5 pgs.
"Medtronic's Corevalve Shows Subclavian Access Success in Patients Contraindicated for Femoral Approach", Medical News Today, May 21, 2009, http://www.medicalnewstoday.com/releases/150929.php, last visited Nov. 24, 2011 1 pg.

(56) References Cited

OTHER PUBLICATIONS

"Medtronic's CoreValve Transcatheter Aortic Valve Replacement System Performs Well in Trial", Medgaget.com article, posted May 20, 2009, http://www.medgadget.com/archives/print/007754print. html, 3 pgs.

"Percutaneous Implantation of the First Repositionable Aortic Valve Prosthesis in a Patent With Severe Aortic Stenosis", L. Buellesfeld, et al., Catheter Cardiovasc Interv. Apr. 1, 2008; 71(5): 579-84, 1 pg.

"Percutaneous Approaches to Aortic Valve Replacement", Adam M. Brodsky, M.D., Applications in Imaging-Cardiac Interventions, Dec. 2004, 6 pgs.

Percutaneous Aortic Valve Implantation: Early Clinical Experience and Future Perspectives:, Danny Dvir, M.D., et al., IMAJ, vol. 11, Apr. 2009, 6 pgs.

"Percutaneous Treatment of Aortic Valve Stenosis", Inder M. Singh, M.D., et al., Cleveland Clinic Journal of Medicine, vol. 75, No. 11, Nov. 2008, 8 pgs.

"First Human Case of Retrograde Transcatheter Implantation of an Aortic Valve Prosthesis", David Paniagua, M.D., et al., Texas Heart Institute Journal, Transcatheter Aortic Valve Prothesis, vol. 32, No. 3, 2005, 6 pgs.

"Percutaneous Transcatheter Aortic Valve Implantation: Assessing Results, Judging Outcomes, and Planning Trials: The Interventionalist Perspective", Paul T.L. Chiam, et al., J. Am. Coll. Cardiol. Intv. 2008: 1; 341-350, 12 pgs.

"Percutaneous Transcatheter Aortic Valve Implantation: Evolution of the Technology", Paul T.L. Chiam, et al., American Heart Journal, Feb. 2009, 229-42, 14 pgs.

First Examination Report for related Australian Application No. 2008325202, dated Nov. 14, 2012, 3 pgs.

First Office Action with English translation for related Chinese Application No. 200880115408.6, dated Mar. 1, 2012, 8 pgs.

Office Action for related European Application No. 08 848 068.6, dated Nov. 26, 2013, 4 pgs.

\* cited by examiner

FIGURE 7
FIGURE 8
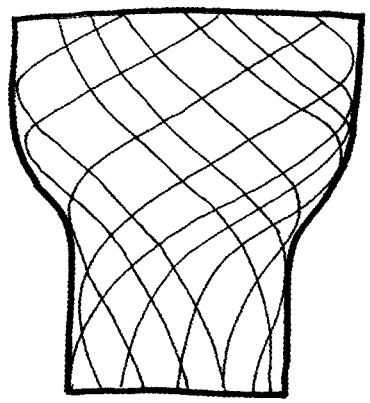
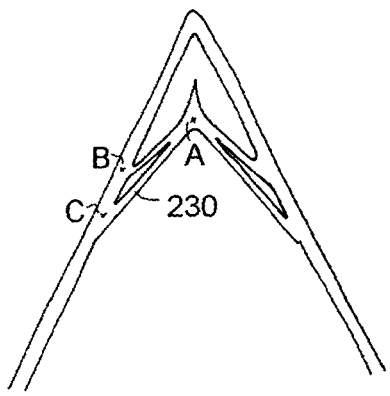
FIGURE 9         FIGURE 10        FIGURE 11
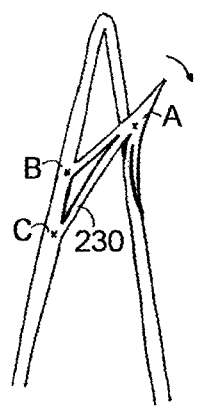  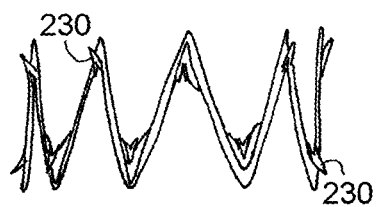

AORTIC VALVE STENT GRAFT

The present patent document is a continuation application that claims the benefit of priority under 35 U.S.C. § 120 of U.S. patent application Ser. No. 13/287,690, filed Nov. 2, 2011 know U.S. Pat. No. 10,105,218), which is a continuation application that claims the benefit of priority under 35 U.S.C. § 120 of U.S. patent application Ser. No. 12/264,740, filed Nov. 4, 2008 (now U.S. Pat. No. 8,715,337), which claims priority under 35 U.S.C. § 119 to U.S. Provisional Patent Application Ser. No. 60/986,908, filed Nov. 9, 2007, each of which is hereby incorporated by reference in its entirety.

PRIORITY CLAIM

This invention claims the benefit of priority of U.S. Provisional Application Ser. No. 60/986,908, entitled "Aortic Valve Stent Graft," filed Nov. 9, 2007, the disclosure of which is hereby incorporated by reference in its entirety.

BACKGROUND

The present embodiments relate to implantable medical devices and methods, and more particularly to an implantable medical device for the repair of a damaged endoluminal valve, such as an aortic valve, and a method for implanting the same.

The aortic valve functions as a one-way valve between the heart and the rest of the body. Blood is pumped from the left ventricle of the heart, through the aortic valve, and into the aorta, which in turn supplies blood to the body. Between heart contractions the aortic valve closes, preventing blood from flowing backwards into the heart.

Damage to the aortic valve can occur from a congenital defect, the natural aging process, and from infection or scarring. Over time, calcium may build up around the aortic valve causing the valve not to open and close properly. Certain types of damage may cause the valve to "leak," resulting in "aortic insufficiency" or "aortic regurgitation." Aortic regurgitation causes extra workload for the heart, and can ultimately result in weakening of the heart muscle and eventual heart failure.

After the aortic valve becomes sufficiently damaged, the valve may need to be replaced to prevent heart failure and death. One current approach involves the use of a balloon-expandable stent to place an artificial valve at the site of the defective aortic valve. Another current approach involves the positioning of an artificial valve at the site of the aortic valve using a self-expanding stent. However, these techniques are imperfect. The normal aortic valve functions well because it is suspended from above through its attachment to the walls of the coronary sinus in between the coronary orifices, and it has leaflets of the perfect size and shape to fill the space in the annulus. These features are difficult to replicate in a percutaneously implanted prosthetic valve. The size of the implantation site depends on the unpredictable effects of the balloon dilation of a heavily calcified native valve and its annulus. Balloon dilation can lead to poor valve function with a persistent gradient or regurgitation through the valve. The diameter of the aortic valve is small and thus the diameter of the dilation is not always predictable, especially with a self-expanding stent. In addition, the shape of the aortic valve is not circular, which can also lead to regurgitation outside the valve.

SUMMARY

The present embodiments provide an endoluminal prosthesis for replacing an aortic valve in a subject. In one embodiment, the prosthesis comprises a first stent, a tubular conduit, and a second stent. The tubular conduit may comprise a valve, wherein at least a portion of the tubular conduit overlaps at least a portion of the first stent. Further, the second stent overlaps at least a portion of the tubular conduit. In use, ones of the first stent, the tubular conduit, and the second stent are coaxially arranged for unidirectionally passing fluid through the prosthesis.

In one embodiment, the first stent comprises a balloon-expandable stent and the second stent comprises a self-expanding stent. The self-expanding stent may at least partially surround the tubular conduit, and the tubular conduit may at least partially surround the balloon-expandable stent. Alternatively, both the balloon-expandable stent and the self-expanding stent may at least partially surround the tubular conduit. The valve may comprise an artificial valve, which may be located at the distal end of the tubular conduit.

In one exemplary method of operation, an endoluminal prosthesis may be introduced into the vascular system. The endoluminal prosthesis comprises a first stent, a tubular conduit comprising a valve, and a second stent, wherein at least a portion of the tubular conduit overlaps at least a portion of the first stent, and at least a portion of the tubular conduit overlaps at least a portion of the second stent. The prosthesis is advanced within the vascular system towards an aortic annulus. Then, at least a portion of the prosthesis is expanded into engagement with the aortic annulus.

The first stent, the tubular conduit and the second stent may be advanced into the vascular system in a sequential manner or simultaneously. In operation, the first stent, the tubular conduit and the second stent may be configured for unidirectionally passing fluid through the prosthesis and substantially or completely inhibiting retrograde flow through the prosthesis.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 7 is an illustration of a braided stent.

FIG. 8 is a top plan view of one embodiment of a barb attached to a stent.

FIG. 9 is a perspective view of the barb attached to a stent of FIG. 8.

FIG. 10 is a side view of one embodiment of a barb.

FIG. 11 is a side view of a portion of a stent with a ring of barbs pointing out from each apex.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
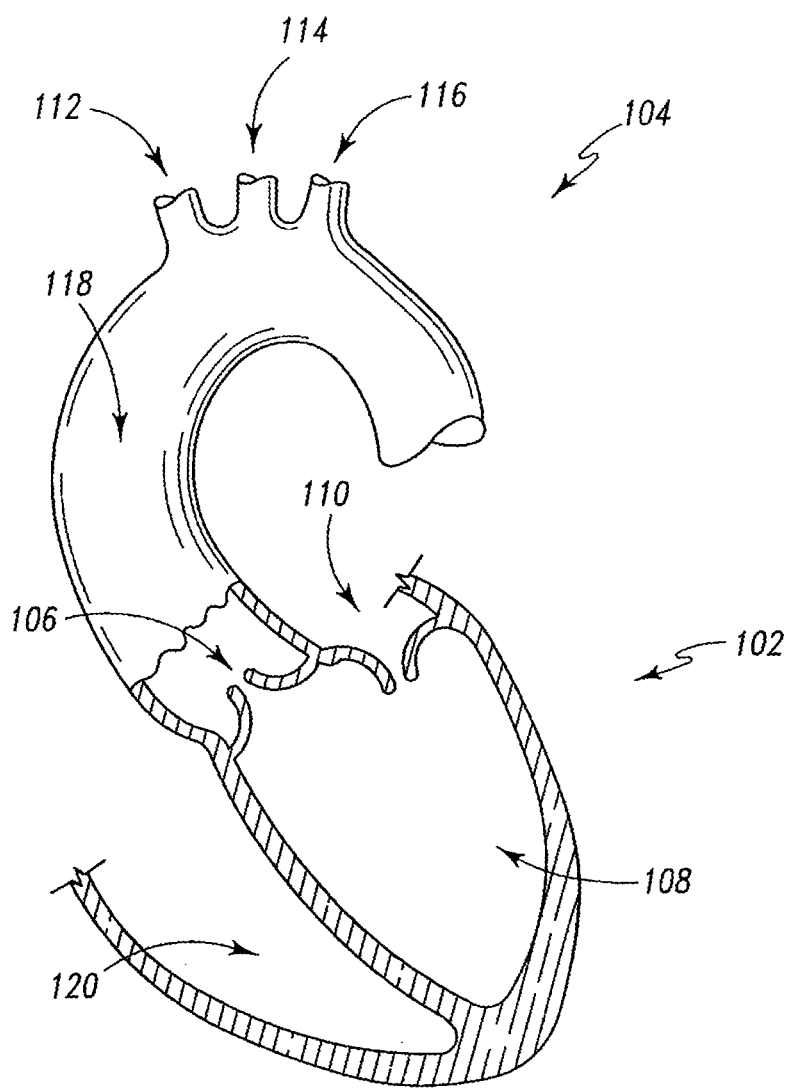
FIG. 1 is a partial cutaway view of a heart and an aorta.

FIG. 1 shows a partial cut-away view of a heart 102 and an aorta 104. The heart 102 may comprise an aortic valve 106 that does not seal properly. This defect of the aortic valve 106 allows blood to flow from the aorta 104 back into the left ventricle 108, leading to a disorder known as aortic regurgitation. A bicuspid mitral valve 110 generally prevents blood from flowing further backwards into the left atrium. Also shown in FIG. 1 are a brachiocephalic trunk 112, a left common carotid artery 114, a left subclavian artery 116, and a right ventricle 120. A portion of the aorta 104 referred to herein as an ascending aorta 118 is shown located between the aortic valve 106 and the brachiocephalic trunk 112.

Figure 2:
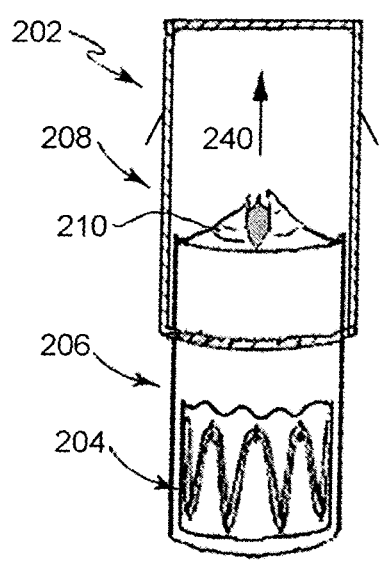
FIG. 2 is a cutaway side view of an endoluminal prosthesis.

FIG. 2 illustrates a first embodiment of a prosthetic device in the form of an aortic stent graft 202. In this embodiment, the aortic stent graft 202 comprises three generally tubular members arranged in coaxial configuration, comprising from inside to outside: a balloon-expandable stent 204, a conduit 206, and a self-expanding stent 208. The conduit 206 includes an artificial valve 210. The artificial valve 210 is shown in an open configuration, allowing unidirectional blood flow through the prosthesis, in the direction indicated by an arrow 240. In this embodiment, the conduit 206 is shown as a thin walled conduit. Also in this embodiment, the artificial valve 210 is shown near a distal end of the conduit 206.

The shape, size, and dimensions of each of the members of the prosthetic device 202 may vary. Consequently, the overall size and shape of the aortic stent graft prosthesis may vary. The size of a preferred prosthetic device is determined primarily by the diameter of the vessel lumen (preferably for a healthy valve/lumen combination) at the intended implant site, as well as the desired length of the overall stent and valve device. Thus, an initial assessment of the location of the natural aortic valve in the patient is determinative of several aspects of the prosthetic design. For example, the location of the natural aortic valve in the patient will determine the dimensions of the stents and the tubular conduit, the type of valve material selected, and the size of deployment vehicle. The length of the self-expanding stent 208 is sufficient enough to overlap with the conduit 206 and extend to engagement with the ascending aorta 118.

In the embodiment shown in FIG. 2, the conduit 206 is shown as completely covering the length of the balloon-expandable stent 204. However, in some embodiments the conduit 206 may only partially cover the length of the balloon-expandable stent 204. What is essential is that the length of the conduit 206 is sufficient to overlap at least a part of the balloon-expandable stent 204, to thereby provide coupling that provides flow of fluid through the prosthesis. Similarly, the length of the self-expanding stent 208 can vary. What is essential is that the length of the self-expanding stent 208 is sufficient to overlap the conduit 206, to thereby provide coupling that provides flow of fluid through the prosthesis.

The tubular members are preferably axially uniform. Furthermore, the tubular members shown in FIG. 2 are presented as roughly cylindrical. In alternative embodiments, one or more of these tubular members may be contoured. For example, one or more of the members may be gradually tapering, i.e., they may be tubular gradually narrowing distally or tubular gradually widening distally. The tubular members may further be elliptical, conical, or have combinations of regular shapes or irregular shapes that conform to the shape of the recipient's anatomy.

Figure 3:
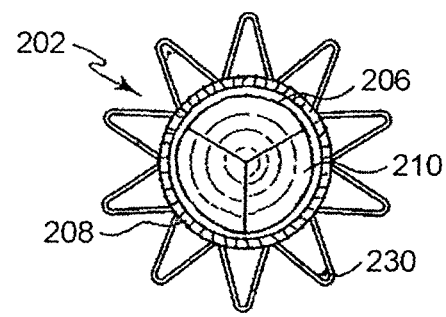
FIG. 3 is a top plan view of the prosthesis of FIG. 2.

FIG. 3 is a top plan view of the prosthesis of FIG. 2, showing the artificial valve 210 in a closed position. In this view, the artificial valve 210 can be seen as attached to the conduit 206. The artificial valve 210 shown in this example includes three leaflets. Also shown in FIG. 3 is the self-expanding stent 208. As can be seen in FIG. 3, the tubular members are presented as coaxial and as roughly cylindrical. As described above, and in alternative embodiments, one or more of these tubular members may be contoured, tapered, conical, or have irregular shapes that conform to the shape of the lumen.

Figure 4:
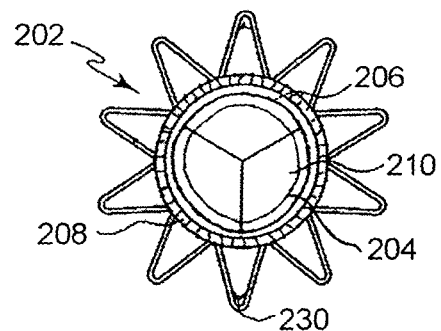
FIG. 4 is a bottom plan view of the prosthesis of FIG. 2.

FIG. 4 is a bottom plan view of the prosthesis of FIG. 2, showing the artificial valve 210 in a closed position. In addition to the conduit 206 and the self-expanding stent 208, this view shows the balloon-expandable stent 204, which is the innermost member.

Figure 5:
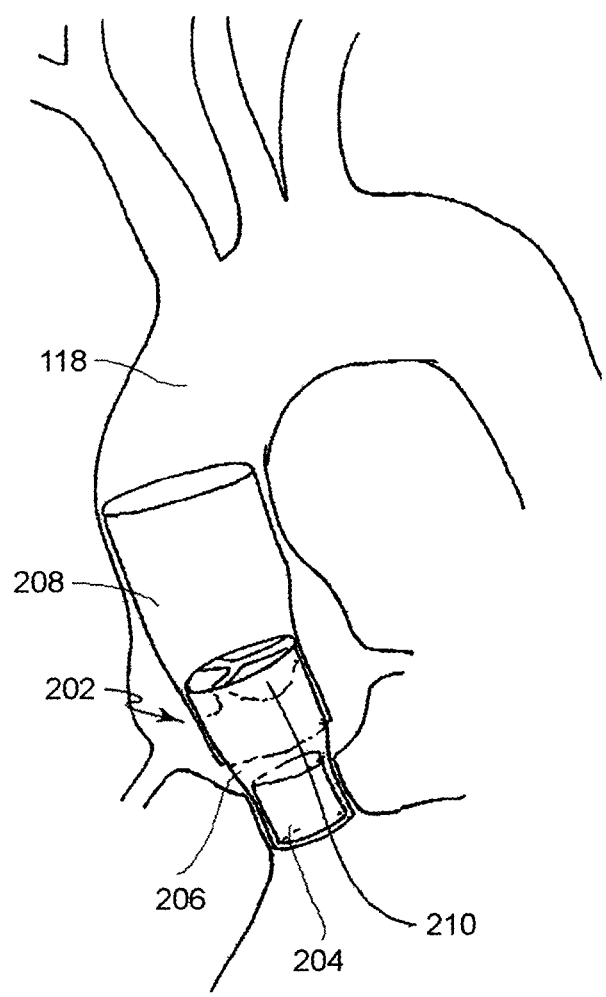
FIG. 5 is a partial cutaway view of an aorta with an implanted prosthesis.
Figure 6:
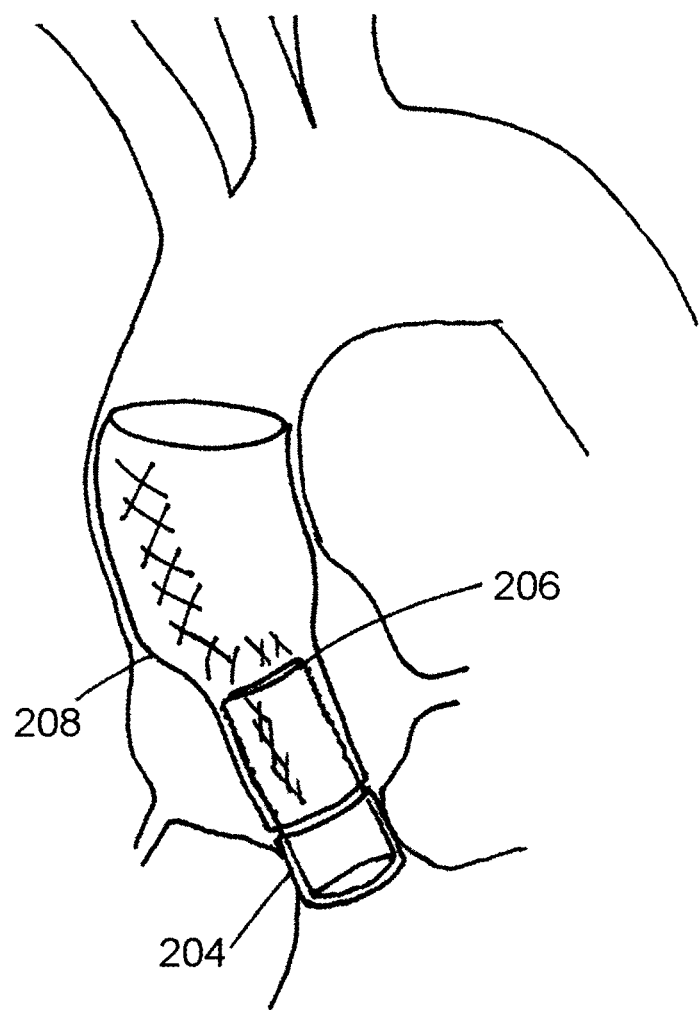
FIG. 6 is another partial cutaway view of an aorta with an implanted prosthesis.

The prosthesis of the present embodiments may be introduced and deployed in a subject's vascular system so that it reaches the aortic annulus, as shown in FIGS. 5 and 6. Preferably, the prosthesis has a compressed state for delivery and an expanded state upon deployment within the artery. Once the prosthesis is deployed and implanted at the site of the aortic annulus, the artificial valve of the prosthesis functionally replaces the aortic valve of the subject. Note the different embodiments of an implanted prosthesis shown in FIGS. 5 and 6. In FIG. 5, the self-expanding stent 208 at least partially surrounds the tubular conduit 206, and the tubular conduit 206 at least partially surrounds the balloon-expandable stent 204. In FIG. 6, both the balloon-expandable stent 204 and the self-expanding stent 208 at least partially surround the tubular conduit 206. In both embodiments, the prosthesis allows unidirectional flow of fluid from the heart into the aorta.

Introduction and deployment of the members that comprise the prosthesis can be simultaneous. In this situation, each of the components may be mounted on a balloon catheter. The balloon is aligned with the aortic annulus, then expanded to substantially simultaneously dilate the aortic annulus and deploy the balloon expandable stent 204 and remainder of the prosthesis. By substantially simultaneously deploying each component of the prosthesis at the same time the annulus is dilated, potentially fatal regurgitation problems may be avoided.

Alternatively, introduction and deployment of the individual members can be sequential. If sequential deployment of the components is provided, a physician may need to stop blood flow due to potentially fatal aortic regurgitation problems associated with dilation of the aortic annulus and subsequent individual insertion of the prosthetic components.

In a further alternative embodiment, the deployment can be a combination of simultaneous and sequential, i.e. some members of the prosthesis can be deployed simultaneously, whereas other or others can be deployed sequentially.

The self-expanding stent 208 included in the prosthesis may be a modified Gianturco "Z stent" or any other form of self-expanding stent. The Z-stent design is preferred for straight sections of the aorta, as it provides both significant radial force as well as longitudinal support.

In certain preferred embodiments, the self-expanding stent 208 can be a braided stent, as illustrated in FIGS. 6 and 7. A long, open mesh stent as depicted in FIGS. 6 and 7 provides the necessary downstream support without the struts that would be required were the valve to be supported via annular attachment alone. The design of this stent requires flexibility, resistance to compressive loading, and an atraumatic interface with the aorta. The self-expanding stent may have two zones, i.e., a lower (proximal) zone of narrow diameter and fixed length (resistance to compression), and an upper (distal) zone of wider diameter and variable length (flexibility). A braided stent, such as a Wallstent, may comprise two such zones by varying the braid angle. If the stent were made of Nitinol, its exact braid shape could be determined by heat setting after the wires had all been bent and joined into the basic shape. The proximal end of the stent can be made more atraumatic by joining the ends of the wires as loops.

Typically, the prosthesis has a circular cross-section when fully expanded, so as to conform to the generally circular cross-section of a blood vessel lumen. In one example, the balloon expandable stent 204 and the self-expanding stent 208 may include struts and acute bends or apices that are arranged in a zigzag configuration in which the struts are set at angles to each other and are connected by the acute bends. The stents may include a curved or hooped portion. The present embodiments can be used with a wide variety of stents, including, but not limited to, shape memory alloy stents, expandable stents, and stents formed in situ. Any stent shape suitable for expansion to fit the pertinent anatomical space may be used.

Preferably, the self-expanding stent 208 is formed from nitinol, stainless steel, or elgiloy. Examples of other materials that may be used to form stents include: carbon or carbon fiber, tantalum, titanium, gold, platinum, inconel, iridium, silver, tungsten, cobalt, chromium, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, or polyhydroxybutyrate valerate. Still other biocompatible metals, alloys, or other biodegradable polymers or mixtures or copolymers may be used.

The aortic stent graft 202 may include a biocompatible graft material attached to at least a portion of any stent. The graft material may be connected to the artificial valve. In one embodiment, the graft material forms a lumen, which lumen is adapted to seal against the wall of the aorta at a site proximal to the aortic annulus. In this embodiment, the blood flows through the lumen of the stent graft and the artificial valve regulates the unidirectional flow of blood through the prosthesis.

The biocompatible graft material is preferably non-porous so that it does not leak under physiologic forces. The graft material is preferably made of woven DACRON® polyester (VASCUTEK® Ltd., Renfrewshire, Scotland, UK). Preferably, the graft material is formed without seams. The tubular graft can be made of any other at least substantially biocompatible material including such fabrics as other polyester fabrics, polytetrafluoroethylene (PTFE), expanded PTFE, and other synthetic materials. Naturally occurring biomaterials, such as collagen, are also highly desirable, particularly a derived collagen material known as extracellular matrix (ECM), such as small intestinal submucosa (SIS). An element of elasticity may be incorporated as a property of the fabric or by subsequent treatments such as crimping. The dimensions of the graft may vary according to the dimensions of the artery that is treated. For each patient, a graft can be selected that has diameters that exceed those of the recipient artery. The stent is relied upon to exert sufficient radial outward force to effect a seal between the graft material and the inner wall of the aorta.

To anchor the aortic stent graft to the wall of the arterial lumen, attachment systems are preferably included on the balloon-expandable stent 204 and/or the self-expanding stent 208. The preferred attachment system includes arterial wall engaging members, for example protrusions or barbs 230, as shown in FIGS. 2-4, 8-11, and 16.

Preferably, sharp metal barbs 230 project outward from the surface of the prosthesis 202. Barbs 230 can be attached to one or more members of the prosthesis 202. In one embodiment, barbs 230 are attached to the self-expanding stent 208. In another embodiment, barbs 230 are attached to a balloon-expandable stent 204. Yet in another embodiment, barbs 230 are attached to both the self-expanding stent 208 and the balloon-expandable stent 204. The barbs 230 point caudally, cranially, or in both directions. The barbs 230 are soldered, brazed, glued to a stent or integrally formed at any point, for example, by etching. The number of barbs is variable. In one embodiment, barbs 230 may extend from the self-expanding stent 208 to engage the ascending aorta arterial wall when deployed, and additional barbs may extend from the balloon-expandable stent 204 to engage the coronary sinus. Aortic stent grafts can be used with and without barbs. In the event barbs are omitted, the stents may be configured so that the radial forces exerted upon the coronary sinus and the ascending aorta are enough to hold the balloon-expandable stent 204 and self-expanding stent 208 in place, respectively.

Referring to FIGS. 8 and 9, the arrow indicates outward deflection of an exemplary barb 230. Point A indicates the apex of the barb 230; points B and C indicate points of attachment of the barb 230 to the stent. As the stent expands upon deployment, ΔAC would have to exceed ΔAB, if the barb 230 were to remain in the plane of the stent. However, the stent material can neither stretch nor conform much. The disparity is resolved by the apex A of the barb 230 moving outwards and downwards, as indicated by the arrows in FIGS. 9 and 10.

In the absence of the balloon, the barb 230 might move into the lumen of the stent. To be sure it moves as planned, the barb 230 can be made so that it starts with a slight outward deflection, as shown in FIGS. 8-11. A sharp apex could be made to function as a barb, especially for a very short stent. In this embodiment, the initial bend is even more important; otherwise, the sharp point can puncture the balloon. In a preferred embodiment, as illustrated in FIG. 11, a stent has barbs 230 pointing out from each apex in an expanded state.

As noted above, the aortic stent graft 202 preferably includes an artificial valve 210. The purpose of this artificial valve 210 is to replace the function of the recipient's native damaged or poorly performing aortic valve. The artificial valve 210 is preferably located at the distal end of the conduit 206, farther from the heart. In one example, the artificial valve 210 can be coupled to the conduit 206 with suture.

The artificial valve 210 preferably includes one or more leaflets. Indeed a tubular conduit, sutured longitudinally to opposite sides of the neck of the self-expanding stent 208 would function as a bicuspid valve. Alternatively, three suture lines would create a tricuspid valve with less redundancy. Preferably, and as shown in FIGS. 2-4, the artificial valve 210 includes three leaflets. The leaflets are arranged in the prosthesis such that the leaflets mimic a naturally occurring aortic valve. The artificial valve 210 "opens" to allow blood flow when the pressure on the proximal side of the artificial valve 210 is greater than pressure on the distal side of the artificial valve. Thus, the artificial valve 210 regulates the unidirectional flow of fluid from the heart into the aorta.

The leaflets of the artificial valve 210 can be fabricated from any at least substantially biocompatible material including such materials as polyester fabrics, polytetrafluoroethylene (PTFE), expanded PTFE, and other synthetic materials known to those of skill in the art. Preferably, the leaflets are fabricated from naturally occurring biomaterials. The leaflets can include a derived collagen material, such as an extracellular matrix. The extracellular matrix can be small intestinal submucosa, stomach submucosa, pericardium, liver basement membrane, urinary bladder submucosa, tissue mucosa, dura mater, or the like.

The normal, native aortic valve is suspended from above through its attachment to the walls of the coronary sinus in between the coronary orifices, and it has leaflets of the perfect size and shape to fill the space in the annulus. While suspended valves resist the forces created by diastolic pressure on closed leaflets through attachment to downstream support, it is also possible to support the membrane "leaflets" of an artificial valve from below, just as the struts of a modern tent support the fabric. This approach is described below and has particular advantages in sites where the base of the valve is wide and suitable sites for downstream anchoring are few.

Various artificial valve designs may be used. These designs preferably have at least two membranes with overlapping holes/slits/flaps so that there is no direct path from one side to the other. In the phase of flow (systole for the aortic valve, diastole for the mitral) the membranes lift from the underlying supports, separate and allow blood to escape through their holes. This works best if the outer membrane(s) is slightly baggier than the inner membrane(s). A wide variety of slots and flaps is possible.

Figure 12:
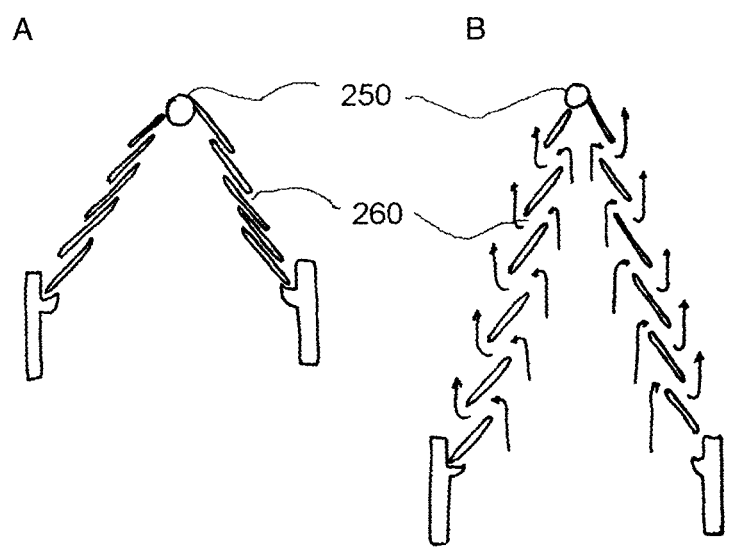
FIGS. 12A-12B illustrate one embodiment of an artificial valve during diastole and systole, respectively.

In the example shown in FIG. 12, the inner membrane has a central hole 250 and the outer membrane has a series of peripheral slits 260 that allow for passage of fluid. In some embodiments, the slits 260 can be almost the whole area of the outer part so that the intervening fabric is just a series of radial tethers. FIG. 12 illustrates the operation of such an artificial valve, during A) diastole, and B) systole. The arrows in FIG. 12B indicate the direction of blood flow through the slits and thus through the valve during systole.

The artificial valve flap need not be a floppy membrane; it could have some rigidity to better support itself in the presence of a rudimentary peripheral attachment mechanism. A single disc could be formed in situ from a spiral ribbon, like a flattened out watch spring. If the whole valve were conical it would transmit the longitudinal forces generated by the pressure gradient of diastole to its edges, where a robust stent would secure the mechanism to the annulus. Separation of the coils layers would allow flow in systole.

Figure 13:
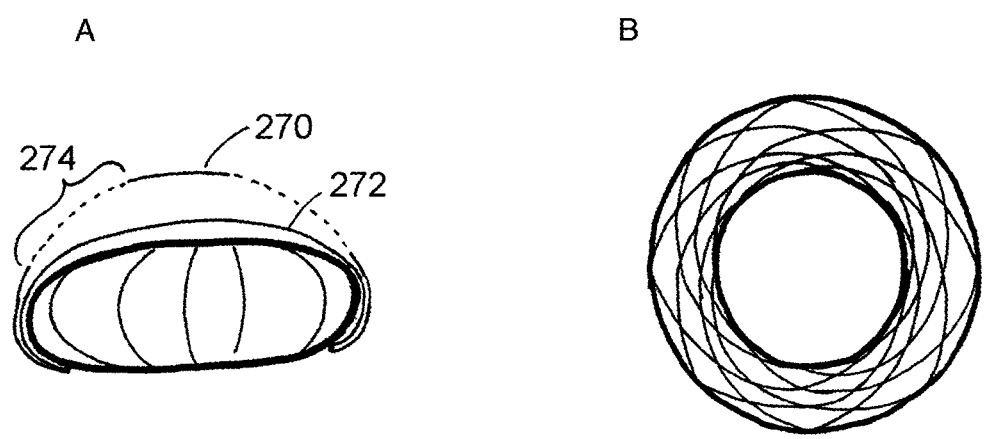
FIGS. 13A-13B are a side view and top view, respectively, of one embodiment of a supportive frame for an artificial valve.
Figure 14:
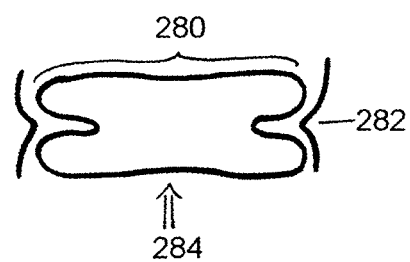
FIG. 14 is an illustration of one example of an artificial valve with a supportive frame.
Figure 15:
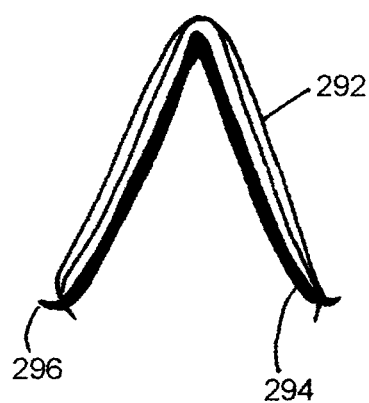
FIG. 15 is an illustration of another example of an artificial valve with a supportive frame.

In some embodiments, the anchoring/support framework for the artificial valve 210 can take a number of shapes, such as cylinder, flattened ball, doughnut, double disc, etc., as illustrated in part in FIGS. 13-15. Of all these, the doughnut may provide more support through tensioning the valve membrane than by direct contact with the membrane's underside. Shown in FIG. 13 is an example of a mesh ball or doughnut, illustrating the positioning of an outer membrane 270, an inner membrane 272, and radial slots 274.

The double disc version, shown in FIG. 14, could be made with a completely impervious covering (no slits or holes), to serve not as a valve but as a baffle or barrier. Indeed, one side of the valve could be thinner than the other to close off some intravascular space. The thin side would sit outside the space and present a smooth, flush surface. The thick side would sit within the space and fill it up, while also providing stability.

Illustrated in FIG. 14 are the valve membranes 280, and the position of the native aortic valve 282. The direction of blood flow is indicated with an arrow 284. The mesh ball valve designs, such as the design shown in FIG. 14, might benefit from having the wires of the weave start and end at the margins of the disc. They would tend to spike the surrounding tissue (or in the case of the double disc, the intervening tissue) and secure the mesh in place.

In general, the supportive frame need not only be a mesh ball or a disc. In some embodiments, the membrane could be conical (tent shaped), e.g. similar to an over-the-wire Greenfield® filter, as shown in FIG. 15. Illustrated in FIG. 15 are the valve membranes 292, the umbrella frame 294, and one or more attachment hooks 296.

The aortic stent graft is introduced into a recipient's vascular system, delivered, and deployed using a deployment device, or introducer. The deployment device delivers and deploys the aortic stent graft within the aorta at a location to replace the aortic valve, as shown in FIGS. 5 and 6. The deployment device may be configured and sized for endoluminal delivery and deployment through a femoral cut-down. Typically, the deployment device includes a cannula or a catheter, capable of having a variety of shapes. The aortic stent graft may be radially collapsed and inserted into the catheter or cannula using conventional methods. In addition to the cannula or catheter, various other components may need to be provided in order to obtain a delivery and deployment system that is optimally suited for its intended purpose. These include and are not limited to various outer sheaths, pushers, stoppers, guidewires, sensors, etc.

Examples of delivery systems for endoluminal devices are known in the art. U.S. Patent Application Publication No. US 2003/0149467 A1 "Methods, Systems and Devices for Delivering Stents" provides examples of available stent delivery systems. Another example of a system and method of delivering endovascular devices was previously described in U.S. Pat. No. 6,695,875 "Endovascular Stent Graft." PCT Patent Publication No. WO098/53761 "A Prosthesis and a Method of Deploying a Prosthesis" discloses an introducer for a prosthesis that retains the prosthesis so that each end can be moved independently. As well, the Zenith® TAA Endovascular Graft uses a delivery system that is commercially available from Cook Inc., Bloomington, Ind.

In one aspect, a trigger wire release mechanism is provided for releasing a retained end of a stent graft and includes a stent graft retaining device, a trigger wire coupling the stent graft to the stent graft retaining device, and a control member for decoupling the trigger wire from the stent graft retaining device. Preferably the trigger wire arrangement includes at least one trigger wire extending from a release mechanism through the deployment device, and the trigger wire is engaged with the proximal end of the aortic stent graft. In a preferred embodiment where the aortic stent graft is modular and includes multiple portions, there can be multiple trigger wires extending from the release mechanism through the deployment device, each of the trigger wires engaging with at least one portion of the aortic stent graft. Preferably, the aortic stent graft includes three members (balloon-expandable stent, conduit, and self-expanding stent). Thus, in one preferred embodiment, three trigger wires individually engage each of these three members of the prosthesis. Individual control of the deployment of each of the members of the prosthesis enables better control of the deployment of the prosthesis as a whole.

Figure 16:
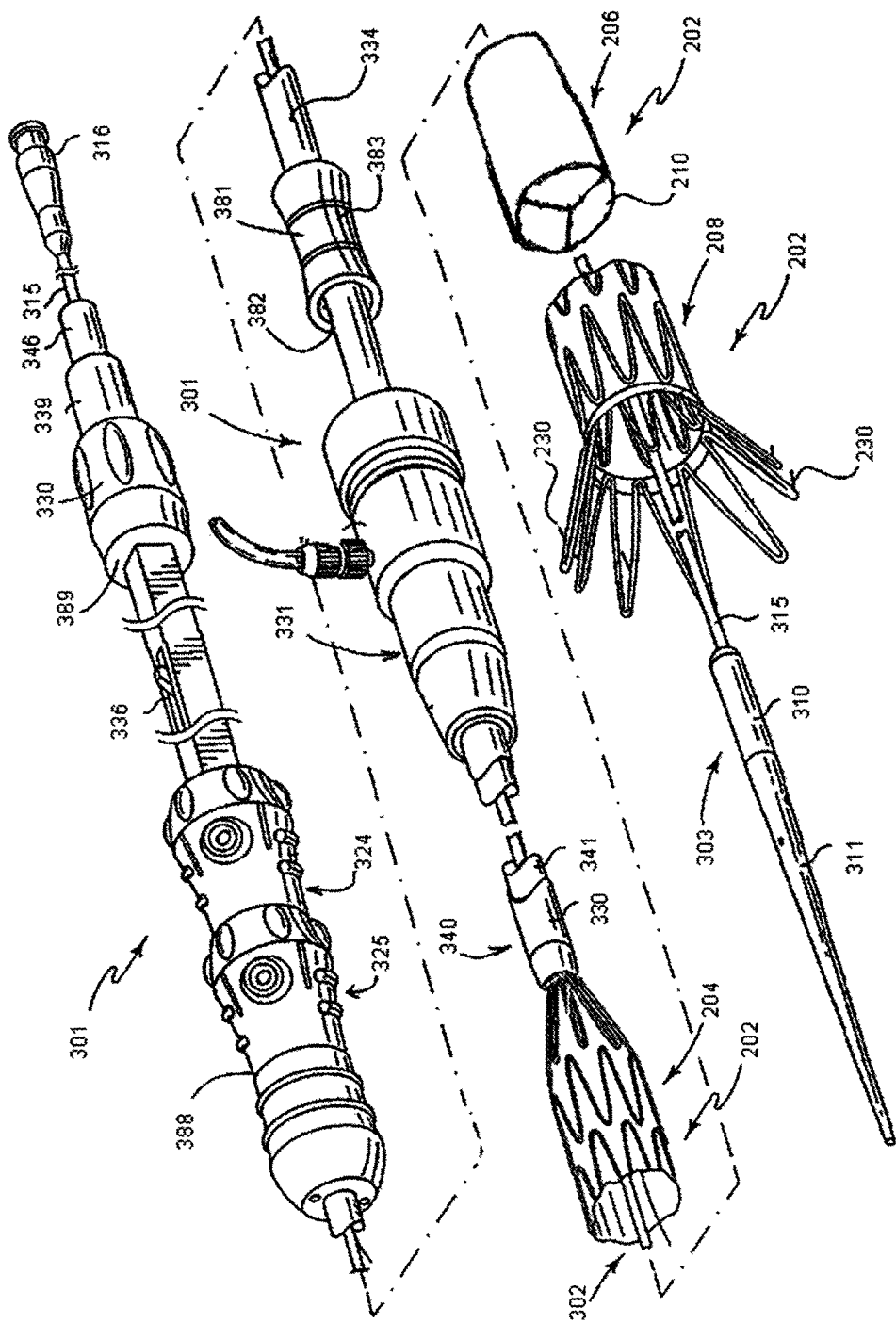
FIG. 16 is a perspective view of selected segments of a deployment device with an aortic stent graft partially deployed.

FIG. 16 shows an exemplary introducer that may be used to deploy the aortic stent graft described above. The introducer is used for deploying an aortic stent graft 202 in an arterial lumen of a patient during a medical procedure. The introducer includes an external manipulation section 301, and a proximal positioning mechanism or attachment region 302. The introducer can also have a distal positioning mechanism or attachment region 303. During a medical procedure to deploy the aortic stent graft, the proximal and distal attachment regions 302 and 303 will travel through the arterial lumen to a desired deployment site. The external manipulation section 301, which is acted upon by a user to manipulate the introducer, remains outside of the patient throughout the procedure.

As illustrated in FIG. 16, the aortic stent graft 202 is retained in a compressed condition by a sheath 330. The sheath 330 can radially compress the aortic stent graft 202 over a distal portion of a thin walled tube 315. The thin walled tube 315 is generally flexible and may include metal. A tube 341, which can be made of plastic, is coaxial with and radially outside the thin walled tube 315. The distal end of the tube 341 is adjacent to the proximal end of the aortic stent graft 202. The tube 341 acts as a pusher to release the stent graft 202 from the introducer during delivery.

The tube 341 is "thick walled", which is to say the thickness of the wall of tube 341 is several times that of the thin walled tube 315. Preferably, the tube 341 is five or more times thicker than the thin walled tube 315. The sheath 330 is coaxial with and is positioned radially outside the thick walled tube 341. The thick walled tube 341 and the sheath 330 extend proximally to the external manipulation region 301, as shown in FIG. 16. The thin walled tube 315 extends to the proximal end of the introducer. The introducer further includes haemostatic sealing means 331 radially disposed about the sheath and the thick walled tube 341. The haemostatic sealing means 331 control the loss of blood through the introducer during a procedure.

The introducer may include an aortic stent graft control member 381 as illustrated in FIG. 16. The stent graft control member 381 is disposed on the dilator portion 334 of the external manipulation section 301. During deployment of the aortic stent graft 202, the sheath 330 is withdrawn proximally over the thick walled tube 341. The haemostatic sealing means 331 generally fits tightly about the sheath 330, resulting in a great amount of friction between the sheath 330 and the thick walled tube 341. As a result, withdrawal of the sheath 330 over the thick walled tube 341 can be difficult. In order to overcome the friction, the operator must have a very tight grip on the thick walled tube 341. Axial positioning of the aortic stent graft 202 may be compromised by the difficulty in gripping the thick walled tube 341. The control member 381 solves this problem by providing the operator with a better grip on the dilator and by decreasing the force that the operator must exert to control and stabilize the thick walled tube 341 during sheath 330 withdrawal. The control member 381 is generally tubular and includes an inner dilator facing surface 382 and an outer grip surface 383. The control member 381 is slidably disposed on the thick walled tube 341 between the haemostatic sealing means 331 and the release wire actuation section to allow the operator to use the control member 381 at any position along the dilator.

The outer grip surface 383 is adapted so that the control member 381 fits the operator's hand comfortably and securely. As such, the outer grip surface 383 may have a diameter that greatly exceeds the diameter of the thick walled tube 341. The outer grip surface 383 may be generally axially uniform. Alternately, the outer grip surface 383 may be generally axially non-uniform, resulting in a contoured gripping surface. FIG. 16 illustrates a control member 381 having a generally non-uniform outer grip surface 383, wherein the control member is generally shaped like an hour glass. The outer grip surface 383 may include a smooth surface finish, or alternately, the outer grip surface may include a rough or textured surface finish. Rough or textured surface finishes are beneficial because they provide increased surface area contact between the operator and the control member 381, thereby increasing the operator's leverage. Multiple surface finishes may be selected to provide various utilitarian and tactile benefits.

The control member 381 is generally deformable so that when the operator grips the control member 381, the control member 381 compresses against the thick walled tube 341. The control member 381 transfers the force exerted by the operator to the thick walled tube 341. The dilator facing surface 382 may include a generally smooth surface. Alternately, the dilator facing surface 382 may have a rough or textured surface. A rough or textured surface may create a more "sticky" or "tacky" contact between the control member 381 and the thick walled tube 341, thereby increasing the force that is transferred by the operator to the dilator.

The dilator facing surface 382 may include a generally uniform surface. Alternately, the dilator facing surface 382 may include a generally non-uniform surface. For example, the dilator gripping surface 382 may include a plurality of engageable projections that extend radially inward towards the thick walled tube 341. When the operator grips the control member 381 against the thick walled tube 341, engageable projections engage the surface of the thick walled tube. Engageable projections increase the surface contact area between the control member 381 and the thick walled tube, thereby increasing the force that the control member transfers from the operator to the thick walled tube 341. Engageable projections may include any geometric or non-geometric shape. For example, engageable projections may include "O" shapes, lines, dashes, "V" shapes, or the like.

The distal attachment region 303 includes a retention device 310. The retention device 310 holds the distal end of the aortic stent graft in a compressed state. The retention device 310 has at its distal end a long tapered flexible extension 311. The flexible extension 311 includes an internal longitudinal aperture which facilitates advancement of the tapered flexible extension 311 along a previously inserted guidewire. The longitudinal aperture also provides a channel for the introduction of medical reagents. For example, it may be desirable to supply a contrast agent to allow angiography to be performed during placement and deployment phases of the medical procedure.

The distal end of the thin walled tube 315 is coupled to the flexible extension 311. The thin walled tube 315 is flexible so that the introducer can be easily advanced. The thin walled tube extends proximally through the introducer to the manipulation section 301, terminating at a connection means 316. The thin walled tube 315 is in mechanical communication with the flexible extension, allowing the operator to axially and rotationally manipulate the distal attachment region 303 with respect to the aortic stent graft 202. The connection means 316 is adapted to accept a syringe to facilitate the introduction of reagents into the thin walled tube 315. The thin walled tube 315 is in fluid communication with the flexible extension 311, which provides for introduction of reagents through the aperture into the arterial lumen.

The trigger wire release actuation section of the external manipulation section 301 includes an elongate body 336. Distal and proximal trigger wire release mechanisms 324, 325 are disposed on the elongate body 336. End caps 338 are disposed on proximal and distal ends of the elongate body 336. End caps 338 include longitudinally-facing laterally opposed surfaces defining distal and proximal stops 388, 389. Distal and proximal trigger wire release mechanisms 324, 325 are slidably disposed on the elongate body 336 between distal and proximal stops 388, 389. Distal and proximal stops 388, 389 retain the distal and proximal trigger wire release mechanisms 324, 325 on the elongate body 336. The actuation section includes a locking mechanism for limiting the axial displacement of trigger wire release mechanisms 324, 325 on the elongate body 336.

Referring to the external manipulation section 301, a pin vise 339 is mounted onto the proximal end of the elongate body 336. The pin vise 339 has a screw cap 346. When screwed in, the vise jaws clamp against (engage) the thin walled metal tube 315. When the vise jaws are engaged, the thin walled tube 315 can only move with the body 336, and hence the thin walled tube 315 can only move with the thick walled tube 341. With the screw cap 346 tightened, the entire assembly can be moved as one with respect to the sheath 330.

The self-expanding stent 208 causes the aortic stent graft 202 to expand during its release from the introducer 301, shown in FIG. 16. The stent graft shown in this example also includes barbs 230 that extend from the distal end of the self-expanding stent 208. When the self-expanding stent 208 is deployed (released), the barbs 230 anchor the distal end of the aortic stent graft 202 to the surrounding lumen (not shown). Upon endoluminal deployment, the balloon-expandable stent 204 is inflated and expanded. Expansion of the balloon-expandable stent can be caused by inflation of the catheter between the sleeves so that the ends of the stent are withdrawn from the respective sleeves and the stent released and expanded into position. The tubular conduit 206 is also expanded upon release from the introducer. When the tubular conduit 206 is positioned between the balloon-expandable stent 204 and the self-expanding stent 208 and is in contact with those two stents, expansion of those two stents 204 and 208 results in expansion of the tubular conduit 206 as well. Preferably, the tubular conduit 206 is thin walled, which aids in its expansion when released.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. An endoluminal prosthesis comprising:
at least one stent; and
a tubular conduit comprising an aortic valve replacement that allows fluid to pass in an upstream to downstream direction, wherein at least a portion of the tubular conduit overlaps at least a portion of the at least one stent,
wherein an outflow end of the tubular conduit terminates at a location between an upstream proximal end and a downstream distal end of the at least one stent,
wherein the at least one stent comprises a proximal zone having a first diameter and a distal zone having a second diameter, where the proximal zone is upstream of the distal zone, where the first diameter is narrower than the second diameter, and there is a taper between the first and second diameters,
wherein a proximal end of the aortic valve replacement is disposed distal to a distal end of the proximal zone, and
wherein a terminal distal-most end of the distal zone comprises a greater diameter than a terminal proximal-most end of the proximal zone.

2. The endoluminal prosthesis of claim 1, wherein the taper of the at least one stent is positioned at least partially downstream of the aortic valve replacement.

3. The endoluminal prosthesis of claim 1, wherein the at least one stent comprises at least one uncovered region to allow fluid to pass radially outside of an outer perimeter of the at least one stent after passing through the aortic valve replacement.

4. The endoluminal prosthesis of claim 1, wherein the at least one stent at least partially surrounds the tubular conduit.

5. The endoluminal prosthesis of claim 1, wherein the at least one stent comprises a balloon-expandable stent.

6. The endoluminal prosthesis of claim 1, wherein the at least one stent comprises a self-expanding stent.

7. The endoluminal prosthesis of claim 1, wherein the aortic valve replacement is located at the distal end of the tubular conduit.

8. The endoluminal prosthesis of claim 1 further comprising one or more barbs.

9. An endoluminal prosthesis comprising:
at least one stent; and
a tubular conduit comprising an aortic valve replacement that allows fluid to pass in an upstream to downstream direction, wherein at least a portion of the tubular conduit overlaps at least a portion of the at least one stent,
wherein an outflow end of the tubular conduit terminates at a location between an upstream proximal end and a downstream distal end of the at least one stent,
wherein the at least one stent comprises a proximal zone having a length of a uniform first diameter and a distal zone having a second diameter, where the proximal zone is upstream of the distal zone, where the first diameter is narrower than the second diameter, and there is a tapered region between the first and second diameters,
wherein the aortic valve replacement is disposed entirely within the tapered region, and wherein a terminal distal-most end of the distal zone comprises a greater diameter than a terminal proximal-most end of the proximal zone.

10. The endoluminal prosthesis of claim 9, wherein the at least one stent comprises at least one uncovered region to allow fluid to pass radially outside of an outer perimeter of the at least one stent after passing through the aortic valve replacement.

11. The endoluminal prosthesis of claim 9, wherein the at least one stent at least partially surrounds the tubular conduit.

12. The endoluminal prosthesis of claim 9, wherein the at least one stent comprises a balloon-expandable stent.

13. The endoluminal prosthesis of claim 9, wherein the at least one stent comprises a self-expanding stent.

14. The endoluminal prosthesis of claim 9, wherein the aortic valve replacement is located at the distal end of the tubular conduit.

15. The endoluminal prosthesis of claim 9 further comprising one or more barbs.

16. An endoluminal prosthesis comprising:
at least one stent; and
a tubular conduit comprising an aortic valve replacement that allows fluid to pass in an upstream to downstream direction, wherein at least a portion of the tubular conduit overlaps at least a portion of the at least one stent,
wherein an outflow end of the tubular conduit terminates at a location between an upstream proximal end and a downstream distal end of the at least one stent,
wherein the at least one stent comprises a proximal zone having a first diameter and a distal zone having a second diameter, where the proximal zone is upstream of the distal zone, where the first diameter is narrower than the second diameter, and there is a taper between the first and second diameters,
wherein the tubular conduit overlaps with both the proximal zone and the taper, but lacks an overlap with the distal zone, and
wherein a proximal end of the aortic valve replacement is positioned distal to a substantially uniform diameter of the proximal zone, wherein the substantially uniform diameter is taken from two cross-sections of the proximal zone that are spaced apart along a longitudinal axis of the prosthesis.

17. The endoluminal prosthesis of claim 16, wherein the aortic valve replacement is disposed entirely within the tapered region.

18. The endoluminal prosthesis of claim 16, wherein the taper of the at least one stent is positioned at least partially downstream of the aortic valve replacement.

19. The endoluminal prosthesis of claim 16, wherein the at least one stent comprises at least one uncovered region to allow fluid to pass radially outside of an outer perimeter of the at least one stent after passing through the aortic valve replacement.

20. The endoluminal prosthesis of claim 16, wherein the aortic valve replacement is located at the distal end of the tubular conduit.

* * * * *